Nov. 26, 1940. J. H. MACPHERSON Plant Pat. 433

AVOCADO TREE

Filed July 10, 1940

INVENTOR
J. H. Macpherson
By Robb & Robb
Attorneys

Patented Nov. 26, 1940 Plant Pat. 433

UNITED STATES PATENT OFFICE

433

AVOCADO TREE

James H. Macpherson, Encinitas, Calif., assignor to himself and Mildred Macpherson, joint tenants Application July 10, 1940, Serial No. 344,821

1 Claim. (Cl. 47—62)

The present invention relates to a new and distinct variety of avocado tree, the result of definite efforts to improve upon the present leading commercial variety known as "Fuerte."

To this end, I planted a large number of seeds from the Fuerte avocado fruit, and the seedlings from all of these seeds were carefully watched and studied until one of them developed into this new and superior variety of avocado having certain definitely desirable characteristics which will be hereinafter more particularly pointed out and recognized as most valuable to the avocado industry.

In the accompanying illustrations:

Figure 1:
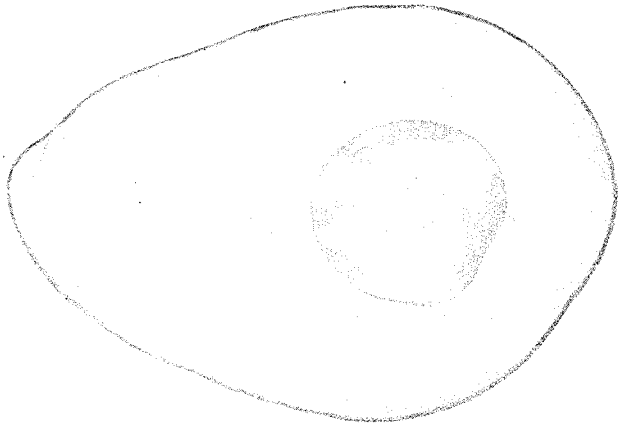
Figure 1 is a longitudinal sectional view through a specimen of the present variety.
Figure 2:
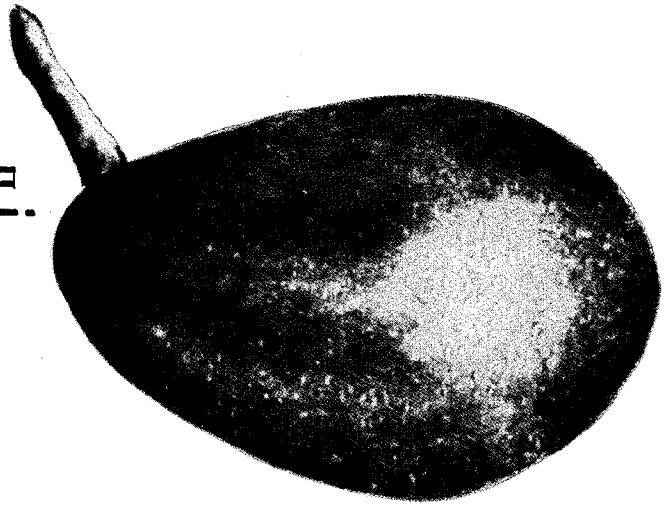
Figure 2 is a view in elevation of the fruit with stem attached.
Figure 3:
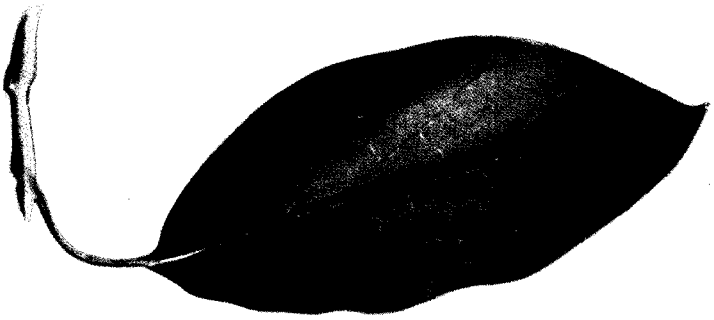
Figure 3 is a plan view of a leaf of the foliage.

Referring first to the distinguishing characteristics of the tree itself, it is noted that it possesses: a strong central trunk extending vertically to the ground and growing substantially ahead of its limbs; secondly, strong horizontal limbs with no drooping as is so characteristic of the known Fuerte variety; thirdly, branches well distributed around the main trunk from top to bottom and a small tight bud with four overlapping bud scales; and lastly, unusual hardiness to cold, having withstood temperatures as low as 24° F.

With respect to the foliage, the mature leaves of the tree of this new variety are elliptical, varying from 4½ to 8 centimeters in width and from 10 to 17 centimeters in length. The leaves are pinnately veined with the mid-rib protruding on the dull undersides of the leaves, while the upper sides are quite smooth. The mature leaves are a dark cress green (Ridgway's, Plate XXXI 29–*m*) with shadings corresponding to those of cress green of Plate XXXI 29–*k* and light cress green 29–*i*.

Since the distinguishing characteristics of this new variety are more apparent in the fruit thereof, they will now be particularly described, it being first desirable to note that the fruit matures through the months from October through March, having particular reference to the vicinity of Encinitas, California, where these observations have been made.

The young fruits produced by the tree of this invention are a dull light green in color. As the fruit matures the background develops an oil green color, similar to that shown on Plate V, 27–*k* of Ridgway's Color Standard, with shadings of colors similar to jade and yew green, Plate XXXI, 27–*k* and *m*, and high-lighted by colors of javel and rainette green, Plate V, 27–*i*, and Plate XXXI, 27–*i*. This background develops a medium number of yellow and rusty spots, on its surface, the size of a pinpoint. The skin of the mature fruit is smooth and leathery. The skin is of medium thickness, slightly thicker than that of the Fuerte fruit, measuring approximately 0.05 centimeter.

The ripe fruit may vary from 4½ inches to 5 inches in length, having a maximum width at the base of 2¾ inches. The weight of the fruit varies from 10 to 12 ounces. A fruit weighing eleven and one-half ounces measured 4¾ inches in length, and 2½ inches in width at the base, and 1¾ inches at the tip. Although the general outside appearance of this fruit resembles that of the Fuerte, the fruit of this invention has the following definite advantages and distinguishing characteristics:

(1) The fruit of this invention is asymmetrical pyriform, having a dorsal ridge, two lateral ridges, and a slight frontal groove.

(2) The flesh or meat has a richer golden yellow color than that of the Fuerte. Immediately under the skin there is a distinctive layer of green flesh, similar to cosse green, Plate V, 29–*i* of Ridgway's Color Standard. The center flesh and that close to the seed is similar to baryta yellow, Plate IV, 21–*f*, with shadings of olive-ocher and mustard yellow, Plate XXX, 21, and Plate XVI, 19–*b*.

(3) The seed of the fruit of this invention averages only one ounce in weight, while the seed of the Fuerte averages 2 ounces in weight.

The fruit of this invention has a very fine flavor and a highly desirable oil content. The oil content of fruits picked and tested in February averaged 19 percent, while those tested in March averaged 23 per cent in oil content. The seed is tight in the cavity and the brown seed coat adheres tightly to the seed.

The fruit stems vary in length from four to ten centimeters, and from 0.08 centimeter to 1 centimeter in width, being about 1 centimeter in width at the bottom. The color of the stems is similar to light cress green, Plate XXXI, 29–*i*, with shadings of cress green and dark cress green, Plates XXXI, 29–*k* and XXXI, 29–*m*, as shown in Ridgeway's Color Standard. The fruit has a tendency to set well back from the terminal buds, thereby receiving considerable protection from the shade of the tree's foliage. The buds of the tree of this invention have two small bud scales and two slightly opposite scales which overlap each other, forming a tight small bud.

It is to be understood that although the description given herein above accurately represents and describes the tree, foliage, and fruit, the general characteristics may vary slightly due to climatic conditions, soil, etc.

A sexual reproduction of this variety establishes that the foregoing characteristics are fixed.

I claim:

A new and distinct variety of avocado tree characterized as to novelty by its habit of growth, its hardiness to cold, the form, size, color, flavor, and oil content of its fruit, the size and weight of the fruit seed, and its ripening period, substantially as shown and described.

JAMES H. MACPHERSON.